United States Patent
Martin et al.

(10) Patent No.: US 9,788,830 B2
(45) Date of Patent: Oct. 17, 2017

(54) NEEDLE CARTRIDGE WITH CAGE

(71) Applicant: Ethicon Endo-Surgery, Inc., Cincinnati, OH (US)

(72) Inventors: David T. Martin, Milford, OH (US); Daniel J. Mumaw, Liberty Township, OH (US); Mark J. Bookbinder, Blue Ash, OH (US); William J. White, West Chester, OH (US); Daniel L. Geiger, Newport, KY (US); Andrew C. Deck, Dayton, OH (US)

(73) Assignee: ETHICON LLC, Guaynabo, PR (US)

( * ) Notice: Subject to any disclaimer, the term of this patent is extended or adjusted under 35 U.S.C. 154(b) by 655 days.

(21) Appl. No.: 14/298,056

(22) Filed: Jun. 6, 2014

(65) Prior Publication Data
US 2015/0351756 A1 Dec. 10, 2015

(51) Int. Cl.
*A61B 17/04* (2006.01)
*A61B 17/00* (2006.01)
*A61B 17/06* (2006.01)

(52) U.S. Cl.
CPC ..... *A61B 17/0469* (2013.01); *A61B 2017/00407* (2013.01); *A61B 2017/00473* (2013.01); *A61B 2017/0608* (2013.01)

(58) Field of Classification Search
CPC ...... A61B 2017/00407; A61B 17/0625; A61B 17/0469; A61B 17/06114
See application file for complete search history.

(56) References Cited

U.S. PATENT DOCUMENTS

| | | | |
|---|---|---|---|
| 1,579,379 | A | 4/1926 | Marbel |
| 1,822,330 | A | 9/1931 | Ainslie |
| 1,884,149 | A | 10/1932 | Nullmeyer |
| 2,291,181 | A | 7/1942 | Alderman |
| 3,168,097 | A | 2/1965 | Dormia |
| 3,598,281 | A | 8/1971 | Watermeier |
| 3,749,238 | A | 7/1973 | Taylor |
| 4,027,608 | A | 6/1977 | Arbuckle |
| 4,123,982 | A | 11/1978 | Bess, Jr. et al. |

(Continued)

FOREIGN PATENT DOCUMENTS

| | | |
|---|---|---|
| DE | 4310315 A1 | 10/1993 |
| EP | 0674875 A1 | 10/1995 |

(Continued)

OTHER PUBLICATIONS

U.S. Appl. No. 13/832,595, filed Mar. 15, 2013 by Ethicon Endo-Surgery, Inc.

(Continued)

*Primary Examiner* — Gregory Anderson
*Assistant Examiner* — Christina Lauer

(57) ABSTRACT

A needle cartridge is adapted to be attached to a receiver on a surgical suturing device. The cartridge comprises an arced needle having a leading end, a trailing end, and a length of suture. A body has a track receiving the needle and defining a circular path. A needle driver is operable to rotate the needle along the circular path. A cover captures the needle in the track. A cage engages and retains the needle cover against the body. The cage may slide relative the body to disengage with a portion of the cover allowing the cover to deflect and release the needle from the track.

3 Claims, 11 Drawing Sheets

(56) References Cited

U.S. PATENT DOCUMENTS

| | | |
|---|---|---|
| 4,196,836 A | 4/1980 | Becht |
| 4,235,177 A | 11/1980 | Arbuckle |
| 4,406,237 A | 9/1983 | Eguchi et al. |
| 4,417,532 A | 11/1983 | Yasukata |
| 4,440,171 A | 4/1984 | Nomoto et al. |
| 4,557,265 A | 12/1985 | Andersson |
| 4,899,746 A | 2/1990 | Brunk |
| 5,133,723 A | 7/1992 | Li et al. |
| 5,209,747 A | 5/1993 | Knoepfler |
| 5,282,806 A | 2/1994 | Haber et al. |
| 5,289,963 A | 3/1994 | McGarry et al. |
| 5,306,281 A | 4/1994 | Beurrier |
| 5,308,353 A | 5/1994 | Beurrier |
| 5,312,023 A | 5/1994 | Green et al. |
| 5,318,578 A | 6/1994 | Hasson |
| 5,383,888 A | 1/1995 | Zvenyatsky et al. |
| 5,389,103 A | 2/1995 | Melzer et al. |
| 5,403,347 A | 4/1995 | Roby et al. |
| 5,403,354 A | 4/1995 | Adams et al. |
| 5,437,681 A | 8/1995 | Meade et al. |
| 5,454,823 A | 10/1995 | Richardson et al. |
| 5,470,338 A | 11/1995 | Whitfield et al. |
| 5,478,344 A | 12/1995 | Stone et al. |
| 5,478,345 A | 12/1995 | Stone et al. |
| 5,480,406 A | 1/1996 | Nolan et al. |
| 5,527,321 A | 6/1996 | Hinchliffe |
| 5,540,704 A | 7/1996 | Gordon et al. |
| 5,540,705 A | 7/1996 | Meade et al. |
| 5,540,706 A | 7/1996 | Aust et al. |
| 5,553,477 A | 9/1996 | Eisensmith et al. |
| 5,554,170 A | 9/1996 | Roby et al. |
| 5,560,532 A | 10/1996 | DeFonzo et al. |
| 5,569,301 A | 10/1996 | Granger et al. |
| 5,571,090 A | 11/1996 | Sherts |
| 5,591,181 A | 1/1997 | Stone et al. |
| 5,593,421 A | 1/1997 | Bauer |
| 5,610,653 A | 3/1997 | Abecassis |
| 5,617,952 A | 4/1997 | Kranendonk |
| 5,630,825 A | 5/1997 | de la Torre et al. |
| 5,632,746 A | 5/1997 | Middleman et al. |
| 5,643,295 A | 7/1997 | Yoon |
| 5,645,552 A | 7/1997 | Sherts |
| 5,649,961 A | 7/1997 | McGregor et al. |
| 5,665,096 A | 9/1997 | Yoon |
| 5,665,109 A | 9/1997 | Yoon |
| 5,669,490 A | 9/1997 | Colligan et al. |
| 5,674,229 A | 10/1997 | Tovey et al. |
| 5,674,230 A | 10/1997 | Tovey et al. |
| 5,693,071 A | 12/1997 | Gorecki et al. |
| 5,702,408 A | 12/1997 | Wales et al. |
| 5,707,379 A | 1/1998 | Fleenor et al. |
| 5,709,693 A | 1/1998 | Taylor |
| 5,713,910 A | 2/1998 | Gordon et al. |
| 5,728,107 A | 3/1998 | Zlock et al. |
| 5,728,108 A | 3/1998 | Griffiths et al. |
| 5,728,109 A | 3/1998 | Schulze et al. |
| 5,733,293 A | 3/1998 | Scirica et al. |
| 5,741,277 A | 4/1998 | Gordon et al. |
| 5,755,729 A | 5/1998 | de la Torre et al. |
| 5,759,188 A | 6/1998 | Yoon |
| 5,766,186 A | 6/1998 | Faraz et al. |
| 5,766,196 A | 6/1998 | Griffiths |
| 5,776,186 A | 7/1998 | Uflacker |
| 5,792,135 A | 8/1998 | Madhani et al. |
| 5,792,151 A | 8/1998 | Heck et al. |
| 5,797,927 A | 8/1998 | Yoon |
| 5,814,054 A | 9/1998 | Kortenbach et al. |
| 5,814,069 A | 9/1998 | Schulze et al. |
| 5,817,084 A | 10/1998 | Jensen |
| 5,846,254 A | 12/1998 | Schulze et al. |
| 5,860,992 A | 1/1999 | Daniel et al. |
| 5,865,836 A | 2/1999 | Miller |
| 5,871,488 A | 2/1999 | Tovey et al. |
| 5,878,193 A | 3/1999 | Wang et al. |
| 5,897,563 A | 4/1999 | Yoon et al. |
| 5,908,428 A | 6/1999 | Scirica et al. |
| 5,911,727 A | 6/1999 | Taylor |
| 5,938,668 A | 8/1999 | Scirica et al. |
| 5,941,430 A | 8/1999 | Kuwabara |
| 5,947,982 A | 9/1999 | Duran |
| 5,954,731 A | 9/1999 | Yoon |
| 5,954,733 A | 9/1999 | Yoon |
| 5,993,466 A | 11/1999 | Yoon |
| 6,016,905 A | 1/2000 | Gemma et al. |
| 6,056,771 A | 5/2000 | Proto |
| 6,071,289 A | 6/2000 | Stefanchik et al. |
| 6,086,601 A | 7/2000 | Yoon |
| 6,096,051 A | 8/2000 | Kortenbach et al. |
| 6,126,666 A | 10/2000 | Trapp et al. |
| 6,129,741 A | 10/2000 | Wurster et al. |
| 6,135,385 A | 10/2000 | Martinez de Lahidalga |
| 6,136,010 A | 10/2000 | Modesitt et al. |
| 6,138,440 A | 10/2000 | Gemma |
| 6,152,934 A | 11/2000 | Harper et al. |
| 6,214,030 B1 | 4/2001 | Matsutani et al. |
| 6,231,565 B1 | 5/2001 | Tovey et al. |
| 6,332,888 B1 | 12/2001 | Levy et al. |
| 6,332,889 B1 | 12/2001 | Sancoff et al. |
| 6,364,888 B1 | 4/2002 | Niemeyer et al. |
| 6,443,962 B1 | 9/2002 | Gaber |
| 6,454,778 B2 | 9/2002 | Kortenbach |
| 6,481,568 B1 | 11/2002 | Cerwin et al. |
| 6,533,112 B2 | 3/2003 | Warnecke |
| 6,719,763 B2 | 4/2004 | Chung et al. |
| 6,719,764 B1 | 4/2004 | Gellman et al. |
| 6,743,239 B1 | 6/2004 | Kuehn et al. |
| 6,755,843 B2 | 6/2004 | Chung et al. |
| 6,783,524 B2 | 8/2004 | Anderson et al. |
| 6,783,537 B1 | 8/2004 | Kuhr et al. |
| D496,997 S | 10/2004 | Dycus et al. |
| 6,923,819 B2 | 8/2005 | Meade et al. |
| 6,936,054 B2 | 8/2005 | Chu |
| 6,939,358 B2 | 9/2005 | Palacios et al. |
| 6,955,643 B2 | 10/2005 | Gellman et al. |
| 7,004,951 B2 | 2/2006 | Gibbens, III |
| 7,022,085 B2 | 4/2006 | Cooke et al. |
| 7,041,111 B2 | 5/2006 | Chu |
| 7,131,979 B2 | 11/2006 | DiCarlo et al. |
| 7,144,401 B2 | 12/2006 | Yamamoto et al. |
| 7,232,447 B2 | 6/2007 | Gellman et al. |
| 7,235,087 B2 | 6/2007 | Modesitt et al. |
| 7,278,563 B1 | 10/2007 | Green |
| 7,338,504 B2 | 3/2008 | Gibbens, III et al. |
| 7,442,198 B2 | 10/2008 | Gellman et al. |
| 7,520,382 B2 | 4/2009 | Kennedy et al. |
| 7,524,320 B2 | 4/2009 | Tierney et al. |
| D594,983 S | 6/2009 | Price et al. |
| 7,582,096 B2 | 9/2009 | Gellman et al. |
| 7,588,583 B2 | 9/2009 | Hamilton et al. |
| 7,615,060 B2 | 11/2009 | Stokes et al. |
| 7,628,796 B2 | 12/2009 | Shelton, IV et al. |
| 7,637,369 B2 | 12/2009 | Kennedy et al. |
| 7,666,194 B2 | 2/2010 | Field et al. |
| 7,686,831 B2 | 3/2010 | Stokes et al. |
| 7,691,098 B2 | 4/2010 | Wallace et al. |
| 7,699,860 B2 | 4/2010 | Huitema et al. |
| 7,703,653 B2 | 4/2010 | Shah et al. |
| 7,763,036 B2 | 7/2010 | Stokes et al. |
| 7,766,925 B2 | 8/2010 | Stokes et al. |
| 7,770,365 B2 | 8/2010 | Enriquez, III et al. |
| 7,806,891 B2 | 10/2010 | Nowlin et al. |
| 7,815,654 B2 | 10/2010 | Chu |
| 7,824,401 B2 | 11/2010 | Manzo et al. |
| 7,828,812 B2 | 11/2010 | Stokes et al. |
| 7,833,235 B2 | 11/2010 | Chu |
| 7,833,236 B2 | 11/2010 | Stokes et al. |
| 7,842,048 B2 | 11/2010 | Ma |
| 7,846,169 B2 | 12/2010 | Shelton, IV et al. |
| 7,857,812 B2 | 12/2010 | Dycus et al. |
| 7,862,572 B2 | 1/2011 | Meade et al. |
| 7,862,575 B2 | 1/2011 | Tal |
| 7,862,582 B2 | 1/2011 | Ortiz et al. |
| D631,965 S | 2/2011 | Price et al. |
| 7,887,554 B2 | 2/2011 | Stokes et al. |

(56) References Cited

U.S. PATENT DOCUMENTS

| | | |
|---|---|---|
| 7,891,485 B2 | 2/2011 | Prescott |
| 7,896,890 B2 | 3/2011 | Ortiz et al. |
| 7,935,128 B2 | 5/2011 | Rioux et al. |
| 7,942,886 B2 | 5/2011 | Alvarado |
| 7,947,052 B2 | 5/2011 | Baxter, III et al. |
| 7,976,553 B2 | 7/2011 | Shelton, IV et al. |
| 7,976,555 B2 | 7/2011 | Meade et al. |
| 7,993,354 B1 | 8/2011 | Brecher et al. |
| 8,012,161 B2 | 9/2011 | Primavera et al. |
| 8,016,840 B2 | 9/2011 | Takemoto et al. |
| 8,021,375 B2 | 9/2011 | Aldrich et al. |
| 8,048,092 B2 | 11/2011 | Modesitt et al. |
| 8,057,386 B2 | 11/2011 | Aznoian et al. |
| 8,066,737 B2 | 11/2011 | Meade et al. |
| 8,100,922 B2 | 1/2012 | Griffith |
| 8,118,820 B2 | 2/2012 | Stokes et al. |
| 8,123,762 B2 | 2/2012 | Chu et al. |
| 8,123,764 B2 | 2/2012 | Meade et al. |
| 8,136,656 B2 | 3/2012 | Kennedy et al. |
| 8,187,288 B2 | 5/2012 | Chu et al. |
| 8,196,739 B2 | 6/2012 | Kirsch |
| 8,206,284 B2 | 6/2012 | Aznoian et al. |
| 8,211,143 B2 | 7/2012 | Stefanchik et al. |
| 8,236,010 B2 | 8/2012 | Ortiz et al. |
| 8,236,013 B2 | 8/2012 | Chu |
| 8,246,637 B2 | 8/2012 | Viola et al. |
| 8,252,008 B2 | 8/2012 | Ma |
| 8,256,613 B2 | 9/2012 | Kirsch et al. |
| 8,257,369 B2 | 9/2012 | Gellman et al. |
| 8,257,371 B2 | 9/2012 | Hamilton et al. |
| 8,292,067 B2 | 10/2012 | Chowaniec et al. |
| 8,292,906 B2 | 10/2012 | Taylor et al. |
| 8,307,978 B2 | 11/2012 | Kirsch et al. |
| 8,333,776 B2 | 12/2012 | Cheng et al. |
| 8,361,089 B2 | 1/2013 | Chu |
| 8,366,725 B2 | 2/2013 | Chu |
| 8,372,090 B2 | 2/2013 | Wingardner et al. |
| 8,398,660 B2 | 3/2013 | Chu et al. |
| 8,460,320 B2 | 6/2013 | Hirzel |
| 8,469,973 B2 | 6/2013 | Meade et al. |
| 8,490,713 B2 | 7/2013 | Furnish et al. |
| 8,500,756 B2 | 8/2013 | Papa et al. |
| 8,512,243 B2 | 8/2013 | Stafford |
| 8,518,058 B2 | 8/2013 | Gellman et al. |
| 8,551,122 B2 | 10/2013 | Lau |
| 8,556,069 B2 | 10/2013 | Kirsch |
| 8,562,630 B2 | 10/2013 | Campbell |
| 8,568,428 B2 | 10/2013 | McClurg et al. |
| 8,579,918 B2 | 11/2013 | Whitfield et al. |
| 8,603,089 B2 | 12/2013 | Viola |
| 8,623,027 B2 | 1/2014 | Price et al. |
| 8,623,048 B2 | 1/2014 | Brecher et al. |
| 8,641,728 B2 | 2/2014 | Stokes et al. |
| 8,663,253 B2 | 3/2014 | Saliman |
| 8,696,687 B2 | 4/2014 | Gellman et al. |
| 8,702,729 B2 | 4/2014 | Chu |
| 8,702,732 B2 | 4/2014 | Woodard, Jr. et al. |
| 8,709,021 B2 | 4/2014 | Chu et al. |
| 8,746,445 B2 | 6/2014 | Kennedy et al. |
| 8,747,304 B2 | 6/2014 | Zeiner et al. |
| D709,194 S | 7/2014 | Millet et al. |
| 8,771,295 B2 | 7/2014 | Chu |
| 8,821,518 B2 | 9/2014 | Saliman et al. |
| 8,821,519 B2 | 9/2014 | Meade et al. |
| D716,945 S | 11/2014 | Miller et al. |
| 8,920,440 B2 | 12/2014 | McClurg et al. |
| 8,920,441 B2 | 12/2014 | Saliman |
| 9,060,769 B2 | 6/2015 | Coleman et al. |
| 9,125,645 B1 | 9/2015 | Martin et al. |
| 9,168,037 B2 | 10/2015 | Woodard, Jr. et al. |
| D745,146 S | 12/2015 | Hess et al. |
| 9,247,938 B2 | 2/2016 | Martin et al. |
| 9,289,206 B2 | 3/2016 | Hess et al. |
| D754,856 S | 4/2016 | Martin et al. |
| 9,314,292 B2 | 4/2016 | Trees et al. |
| 9,351,754 B2 | 5/2016 | Vakharia et al. |
| 9,357,998 B2 | 6/2016 | Martin et al. |
| 9,370,354 B1 | 6/2016 | Martin et al. |
| 9,375,212 B2 | 6/2016 | Martin et al. |
| 9,398,905 B2 | 7/2016 | Martin |
| 9,427,227 B2 | 8/2016 | Martin et al. |
| 9,427,228 B2 | 8/2016 | Hart |
| 9,474,522 B2 | 10/2016 | Deck et al. |
| D771,811 S | 11/2016 | Reyhan et al. |
| 9,486,209 B2 | 11/2016 | Martin et al. |
| 9,498,207 B2 | 11/2016 | Martin et al. |
| 9,526,495 B2 | 12/2016 | Martin et al. |
| 9,554,793 B2 | 1/2017 | Lane et al. |
| 2001/0027312 A1 | 10/2001 | Bacher et al. |
| 2002/0138084 A1 | 9/2002 | Weber |
| 2002/0193809 A1 | 12/2002 | Meade et al. |
| 2003/0083674 A1 | 5/2003 | Gibbens, III |
| 2003/0208100 A1 | 11/2003 | Levy |
| 2003/0233104 A1 | 12/2003 | Gellman et al. |
| 2004/0050721 A1 | 3/2004 | Roby et al. |
| 2004/0172047 A1 | 9/2004 | Gellman et al. |
| 2004/0260314 A1 | 12/2004 | Lizardi et al. |
| 2005/0015101 A1 | 1/2005 | Gibbens, III et al. |
| 2005/0216038 A1 | 9/2005 | Meade et al. |
| 2006/0036232 A1 | 2/2006 | Primavera et al. |
| 2006/0047309 A1 | 3/2006 | Cichocki, Jr. |
| 2006/0069396 A1* | 3/2006 | Meade .............. A61B 17/0482 606/144 |
| 2006/0111732 A1 | 5/2006 | Gibbens et al. |
| 2006/0173491 A1 | 8/2006 | Meade et al. |
| 2006/0259073 A1 | 11/2006 | Miyamoto et al. |
| 2006/0281970 A1 | 12/2006 | Stokes et al. |
| 2006/0282096 A1 | 12/2006 | Papa et al. |
| 2006/0282097 A1 | 12/2006 | Ortiz et al. |
| 2006/0282098 A1 | 12/2006 | Shelton, IV et al. |
| 2006/0282099 A1 | 12/2006 | Stokes et al. |
| 2007/0088372 A1 | 4/2007 | Gellman et al. |
| 2007/0162052 A1 | 7/2007 | Hashimoto et al. |
| 2007/0173864 A1 | 7/2007 | Chu |
| 2007/0256945 A1 | 11/2007 | Kennedy et al. |
| 2008/0091220 A1 | 4/2008 | Chu |
| 2008/0103357 A1 | 5/2008 | Zeiner et al. |
| 2008/0109015 A1 | 5/2008 | Chu et al. |
| 2008/0132919 A1 | 6/2008 | Chui et al. |
| 2008/0177134 A1 | 7/2008 | Miyamoto et al. |
| 2008/0228204 A1 | 9/2008 | Hamilton et al. |
| 2008/0243146 A1 | 10/2008 | Sloan et al. |
| 2008/0255590 A1 | 10/2008 | Meade et al. |
| 2009/0024145 A1 | 1/2009 | Meade et al. |
| 2009/0205987 A1 | 8/2009 | Kennedy et al. |
| 2009/0209980 A1 | 8/2009 | Harris |
| 2009/0248041 A1 | 10/2009 | Williams et al. |
| 2009/0259092 A1 | 10/2009 | Ogdahl et al. |
| 2009/0287226 A1 | 11/2009 | Gellman et al. |
| 2009/0312772 A1 | 12/2009 | Chu |
| 2010/0010512 A1 | 1/2010 | Taylor et al. |
| 2010/0016866 A1 | 1/2010 | Meade et al. |
| 2010/0023024 A1 | 1/2010 | Zeiner et al. |
| 2010/0036415 A1 | 2/2010 | Cabezas |
| 2010/0042116 A1 | 2/2010 | Chui et al. |
| 2010/0063519 A1 | 3/2010 | Park et al. |
| 2010/0078336 A1 | 4/2010 | Reyhan et al. |
| 2010/0100125 A1 | 4/2010 | Mahadevan |
| 2010/0152751 A1 | 6/2010 | Meade et al. |
| 2010/0274265 A1 | 10/2010 | Wingardner et al. |
| 2011/0028999 A1 | 2/2011 | Chu |
| 2011/0040308 A1 | 2/2011 | Cabrera et al. |
| 2011/0042245 A1 | 2/2011 | McClurg et al. |
| 2011/0046642 A1 | 2/2011 | McClurg et al. |
| 2011/0046667 A1 | 2/2011 | Culligan et al. |
| 2011/0060352 A1 | 3/2011 | Chu |
| 2011/0082476 A1 | 4/2011 | Furnish et al. |
| 2011/0288582 A1 | 11/2011 | Meade et al. |
| 2011/0295278 A1 | 12/2011 | Meade et al. |
| 2012/0004672 A1 | 1/2012 | Giap et al. |
| 2012/0035626 A1 | 2/2012 | Chu |
| 2012/0041456 A1 | 2/2012 | Gellman et al. |
| 2012/0055828 A1 | 3/2012 | Kennedy et al. |
| 2012/0059396 A1 | 3/2012 | Harris et al. |

(56) References Cited

U.S. PATENT DOCUMENTS

| | | |
|---|---|---|
| 2012/0109163 A1 | 5/2012 | Chu et al. |
| 2012/0123471 A1 | 5/2012 | Woodard, Jr. et al. |
| 2012/0130404 A1 | 5/2012 | Meade et al. |
| 2012/0143248 A1 | 6/2012 | Brecher et al. |
| 2012/0165837 A1 | 6/2012 | Belman et al. |
| 2012/0165838 A1 | 6/2012 | Kobylewski et al. |
| 2012/0215234 A1 | 8/2012 | Chowaniec et al. |
| 2012/0226292 A1 | 9/2012 | Hirzel |
| 2012/0228163 A1 | 9/2012 | Kirsch |
| 2012/0232567 A1 | 9/2012 | Fairneny |
| 2012/0283748 A1 | 11/2012 | Ortiz et al. |
| 2012/0283750 A1 | 11/2012 | Saliman et al. |
| 2012/0283755 A1 | 11/2012 | Gellman et al. |
| 2013/0041388 A1 | 2/2013 | Lane et al. |
| 2013/0282027 A1 | 10/2013 | Woodard, Jr. et al. |
| 2013/0282031 A1 | 10/2013 | Woodard, Jr. et al. |
| 2013/0296889 A1 | 11/2013 | Tong et al. |
| 2013/0331866 A1 | 12/2013 | Gellman et al. |
| 2014/0005681 A1 | 1/2014 | Gee et al. |
| 2014/0088621 A1 | 3/2014 | Krieger et al. |
| 2014/0166514 A1 | 6/2014 | Martin et al. |
| 2014/0171977 A1 | 6/2014 | Martin et al. |
| 2014/0171978 A1 | 6/2014 | Martin |
| 2014/0171979 A1 | 6/2014 | Martin et al. |
| 2014/0172015 A1 | 6/2014 | Martin et al. |
| 2015/0127024 A1 | 5/2015 | Berry |
| 2015/0133967 A1 | 5/2015 | Martin |
| 2015/0351745 A1 | 12/2015 | Mumaw et al. |
| 2015/0351746 A1 | 12/2015 | Martin et al. |
| 2015/0351749 A1 | 12/2015 | Martin et al. |
| 2016/0345958 A1 | 12/2016 | Martin et al. |
| 2016/0346827 A1 | 12/2016 | Martin et al. |
| 2016/0367238 A1 | 12/2016 | Deck et al. |
| 2016/0367243 A1 | 12/2016 | Martin et al. |

FOREIGN PATENT DOCUMENTS

| | | |
|---|---|---|
| EP | 0739184 B1 | 9/1998 |
| EP | 1791476 A2 | 6/2007 |
| EP | 2055243 A2 | 5/2009 |
| EP | 2292157 A2 | 3/2011 |
| EP | 2308391 A1 | 4/2011 |
| EP | 2792308 A2 | 10/2014 |
| FR | 2540377 A1 | 8/1984 |
| GB | 18602 A | 0/1909 |
| GB | 2389313 A | 12/2003 |
| JP | 55-151956 A | 11/1980 |
| WO | WO 95/19149 A1 | 7/1995 |
| WO | WO 97/29694 A1 | 8/1997 |
| WO | WO 99/12482 A1 | 3/1999 |
| WO | WO 99/40850 A1 | 8/1999 |
| WO | WO 99/47050 A2 | 9/1999 |
| WO | WO 01/12084 A1 | 2/2001 |
| WO | WO 02/102226 A2 | 12/2002 |
| WO | WO 03/028541 A2 | 4/2003 |
| WO | WO 2004/012606 A1 | 2/2004 |
| WO | WO 2004/021894 A1 | 3/2004 |
| WO | WO 2004/086986 A1 | 10/2004 |
| WO | WO 2006/034209 A2 | 3/2006 |
| WO | WO 2007/089603 A2 | 8/2007 |
| WO | WO 2008/045333 A2 | 4/2008 |
| WO | WO 2008/045376 A2 | 4/2008 |
| WO | WO 2008/081474 A1 | 7/2008 |
| WO | WO 2008/147555 A2 | 12/2008 |
| WO | WO 2008/150773 A1 | 12/2008 |
| WO | WO 2010/031064 A1 | 3/2010 |
| WO | WO 2010/062380 A2 | 6/2010 |
| WO | WO 2010/127274 A1 | 11/2010 |
| WO | WO 2011/156733 A2 | 12/2011 |
| WO | WO 2012/029689 A1 | 3/2012 |
| WO | WO 2012/044998 A2 | 4/2012 |
| WO | WO 2012/068002 A1 | 5/2012 |
| WO | WO 2012/088232 A3 | 6/2012 |
| WO | WO 2013/142487 A1 | 9/2013 |
| WO | WO 2013/158622 A1 | 10/2013 |
| WO | WO 2014/147619 A1 | 9/2014 |
| WO | WO 2014/162434 A1 | 10/2014 |

OTHER PUBLICATIONS

U.S. Appl. No. 13/832,660, filed Mar. 15, 2013 by Ethicon Endo-Surgery, Inc.
U.S. Appl. No. 13/832,709, filed Mar. 15, 2013 by Ethicon Endo-Surgery, Inc.
U.S. Appl. No. 13/832,786, filed Mar. 15, 2013 by Ethicon Endo-Surgery, Inc.
U.S. Appl. No. 13/832,816, filed Mar. 15, 2013 by Ethicon Endo-Surgery, Inc.
U.S. Appl. No. 13/832,867, filed Mar. 15, 2013 by Ethicon Endo-Surgery, Inc.
U.S. Appl. No. 13/832,897, filed Mar. 15, 2013 by Ethicon Endo-Surgery, Inc.
U.S. Appl. No. 13/832,986, filed Mar. 15, 2013 by Ethicon Endo-Surgery, Inc.
U.S. Appl. No. 13/833,042, filed Mar. 15, 2013 by Ethicon Endo-Surgery, Inc.
U.S. Appl. No. 13/833,121, filed Mar. 15, 2013 by Ethicon Endo-Surgery, Inc.
Endo 360 "Laparoscopic & Minimally Invasive Suturing Devices" Catalog—2 Pages—EndoEvolution, LLC—2011.
Covidien Endo Stitch (Features and Benefits) "Suturing Made Easy" Brochure—4 Pages—2008.
Pages from www.endoevolution.com. Printed on Jun. 3, 2014, but publication date unknown. Please treat as prior art until applicant establishes otherwise.
U.S. Appl. No. 13/792,976, filed Mar. 11, 2013 by Ethicon Endo-Surgery, Inc.
U.S. Appl. No. 14/298,083, filed Jun. 6, 2014 by Ethicon Endo-Surgery, Inc.
U.S. Appl. No. 14/600,486, filed Jan. 20, 2015 by Ethicon Endo-Surgery, Inc.
U.S. Appl. No. 29/493,233, filed Jun. 6, 2014 by Ethicon Endo-Surgery, Inc.
U.S. Appl. No. 14/741,849, filed Jun. 17, 2015 by Ethicon Endo-Surgery, Inc.
U.S. Appl. No. 29/530,605, filed Jun. 18, 2015 by Ethicon Endo-Surgery, Inc.
International Preliminary Report Dated Jun. 16, 2015, International Application No. PCT/US2013/074866.
International Search Report Dated May 6, 2014, International Application No. PCT/US2013/074866.
International Search Report Dated Sep. 15, 2015, International Application No. PCT/US2015/031883.
International Preliminary Report Dated Dec. 6, 2016, International Application No. PCT/US2015/031883.
International Search Report Dated Sep. 28, 2015, International Application No. PCT/US2015/031911.
International Search Report Dated Aug. 8, 2016, International Application No. PCT/US2016/033782.
International Search Report Dated Jul. 29, 2016, International Application No. PCT/US2016/035390.
International Search Report Dated Nov. 14, 2016, International Application No. PCT/US2016/037348.
International Search Report Dated Nov. 14, 2016, International Application No. PCT/US2016/037350.
International Search Report Dated Oct. 24, 2016, International Application No. PCT/US2016/037557.
European Search Report Dated Feb. 3, 2016; Application No. 15176794.4.
European Search Report Dated Dec. 7, 2015; Application No. 15176796.9.
European Search Report Dated Dec. 4, 2015; Application No. 15176924.7.

(56) References Cited

OTHER PUBLICATIONS

European Search Report Dated Nov. 30, 2015; Application No. 15176774.6.

* cited by examiner

NEEDLE CARTRIDGE WITH CAGE

BACKGROUND

The present invention relates in general to surgical devices and procedures, and more particularly to surgical suturing.

Sutures are often used in a wide variety of surgical procedures. Manual suturing is typically accomplished by the surgeon using a fine pair of graspers to grab and hold a suture needle, pierce the tissue with the needle, let go of the needle, and regrasp the needle to pull the needle and accompanying suture thread through the tissues to be sutured. Such needles are typically curved with the suture attached to the trailing end of the needle. A variety of automated suturing devices have been attempted to speed the process of suturing and to facilitate fine suturing or suturing during endoscopic, laparoscopic, or arthroscopic surgeries. While automated suturing devices are generally known, no one has previously made or used a surgical suturing device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrate some non-limiting examples of the invention. Unless otherwise indicated, the figures are not necessarily drawn to scale, but rather to illustrate the principles of the invention.

SUMMARY

Figure 1:
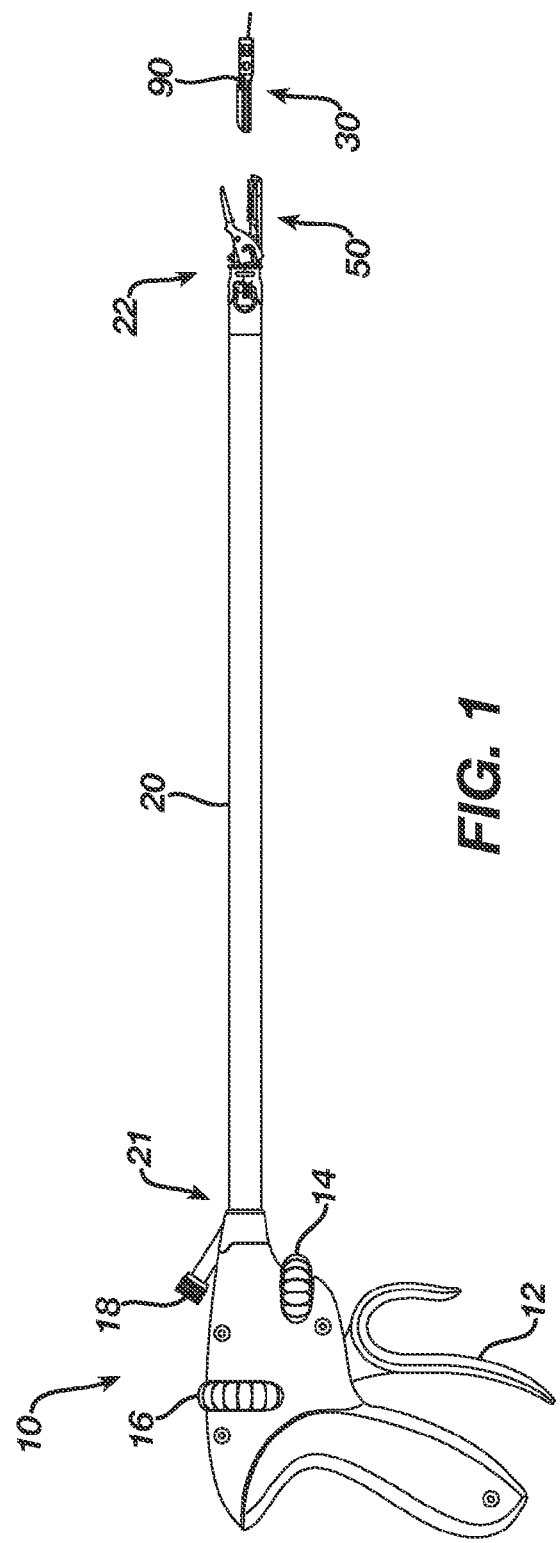
FIG. 1 depicts a side view of a surgical suturing device.

In one embodiment, a surgical suturing device comprises an arced needle having a leading end, a trailing end, and a length of suture. A needle driver is operable to drive the needle in a first rotational direction along a circular path. A cleat projects into the circular path and is operable to engage and prevent the needle from rotating in a second rotational direction opposite the first rotational direction. The cleat may project inward into the plane of the circular path.

In another embodiment, a needle cartridge is adapted to be attached to a receiver on a surgical suturing device. The cartridge comprises an arced needle having a leading end, a trailing end, and a length of suture. A track receives the needle and defines a circular path. A needle driver is operable to rotate the needle along the circular path in a first rotational direction. A cover captures the needle in the track. The cover comprises an outer face, an inner face, and a cleat projecting from the inner face into the track. The cleat is adapted to engage the trailing end of the needle and prevent the needle from rotating in a second rotational direction opposite the first rotational direction.

The needle driver may reciprocate between a drive stroke and a return stroke. The drive stroke may rotate the needle about 180 degrees. The cover may comprise two cleats projecting into the track spaced about 180 degrees from one another along the circular path. The cleats may be positioned to be adjacent the trailing end of the needle at the end of the drive strokes. The cleat and cover may be monolithically formed. The cleat may dimensionally interfere with the needle in the needle track. The cover may resiliently deflect to accommodate the interference. The upper face of the cover may comprise reliefs aligned with the cleats. The cleat may comprise a ramped leading face and a stepped trailing face adapted to engage the trailing end of the needle.

In another embodiment, a surgical suturing device comprises an arced needle comprising a leading end, a trailing end, and a length of suture connected to the needle. A needle driver is adapted to engage and rotate the needle in a circular path in a first rotational direction. A means engages the needle and prevents the needle from rotating in a second rotational direction opposite of the first rotational direction.

In yet another embodiment, a needle cartridge is adapted to be attached to a receiver on a surgical suturing device. The cartridge comprises an arced needle having a leading end, a trailing end, and a length of suture. A body has a track receiving the needle and defining a circular path. A needle driver is operable to rotate the needle along the circular path. A cover captures the needle in the track. A cage engages and retains the needle cover against the body. The cage may slide relative the body to disengage with a portion of the cover allowing the cover to deflect and release the needle from the track.

In another embodiment, a needle cartridge is adapted to be attached to a receiver on a surgical suturing device. The cartridge comprises an arced needle having a leading end, a trailing end, and a length of suture. A body has a pair of distally projecting arms and a track receiving the needle and defining a circular path. A needle driver is operable to rotate the needle along the circular path across the body arms. A cover captures the needle in the track, the cover having a pair of distally projecting arms aligned with the body arms. A cage is slideable relative the body between a distal position where the cage constrains the cover arms against the body arms to capture the needle in the track, and a proximal position where the cage disengages from the cover arms allowing the needle to eject from the track. The body and cover arms may define a generally U-shaped distal end, and the cage may comprise a U-shaped distal end that aligns with the U-shaped distal end when the cage is in its distal position. The cover arms deflect to eject the needle.

In yet another embodiment, a needle cartridge is adapted to be attached to a receiver on a surgical suturing device. The cartridge comprises an arced needle having a leading end, a trailing end, and a length of suture. A cartridge body has a track that receives the needle and defining a circular path. A needle driver is operable to rotate the needle along the circular path. A cover is on the body and positioned over the needle in the track. The cover is selectively moveable relative to the body to release the needle from the track.

The needle cartridge may further comprise a hinge connecting the cover to the body. The body may have a longitudinal axis and the hinge is oriented normal to the longitudinal axis. The hinge is oriented parallel to the longitudinal axis. The needle cartridge may further comprise a pivot connecting the cover to the body. The cover may rotate about the pivot in a plane parallel with the circular path. The cover may slide laterally relative the body.

In another embodiment, a needle cartridge is adapted to be attached to a receiver on a surgical suturing device. The cartridge comprises an arced needle having a leading end, a trailing end, and a length of suture. A cartridge body has a track that receives the needle and defining a circular path. A needle driver is operable to rotate the needle along the circular path. A cover is on the body positioned over the needle in the track. The cartridge comprises a means for moving the cover to release the needle from the track.

In yet another embodiment, a needle cartridge is adapted to be attached to a receiver on a surgical suturing device. The cartridge comprises a body having a length, a width, and a height. The length is at least twice the width, and the width is less than 3.5 times the height. The cartridge comprises an arced needle and a suture, and a needle driver operable to drive the needle in a circular path. The length may be less than 5 times with width, and the width may be greater than the height.

The needle cartridge may further comprise one or more asymmetrical features operable to prevent improper engagement with the receiver. The needle cartridge may further comprise a transmission connecting a rotary input to the needle driver. The needle cartridge may further comprise a step operable to be engaged by a latch tooth on the receiver. The body may further comprise upper and lower faces being generally flat and parallel to one another.

In another embodiment, a needle cartridge adapted to be attached to a receiver on a surgical suturing device. The cartridge comprises a generally flat upper and lower faces parallel to one another, a proximal end and two distal arms. The cartridge has a length, a width and a height wherein the length is at least twice the width, and the width is less than 3.5 times the height. The cartridge has an arced needle and a suture, and a needle driver operable to drive the needle in a circular path spanning the arms. The length may be less than 5 times with width, and the width may be greater than the height The upper and lower surfaces may be asymmetrical to prevent improper engagement with the receiver. The distal face may be asymmetrical to prevent improper engagement with the receiver. A recessed step on the upper face may be operable to be engaged by a latch tooth on the receiver. A rotary input on the lower face and a transmission may operably connect the rotary input to the needle driver.

In another embodiment, a needle cartridge is adapted to be attached to a receiver on a surgical suturing device. The cartridge comprises upper and lower faces each being generally flat and parallel to one another. The upper and lower faces are each generally rectangular with a U-shaped distal notch. The upper and lower faces each have a length and a width where the length is at least twice the width. The cartridge has an arced needle and a suture, and a needle driver operable to drive the needle in a circular path parallel with the upper and lower faces and across the U-shaped notch. A transmission operably connects the rotary input on the lower face to the needle driver.

DETAILED DESCRIPTION

FIG. 1 illustrates an embodiment of a surgical suturing device. An elongate shaft (20) has a proximal end (21), a distal end (22), and a longitudinal axis extending therebetween. An actuator (10) is connected to the proximal end (21) of the shaft (20). In this embodiment the actuator (10) is a manual pistol grip handle; however, a variety of other manual actuators could also be used, including a scissor grip handle, a syringe grip handle, endoscopic rotary knobs, and the like. The actuator (10) could also take the form of a robotic interface, such as a DAVINCI puck, or a housing comprising gears or pulleys, servomechanisms, and the like.

A circular needle applier (30) is connected to the distal end (22) of the shaft (20). The circular needle applier (30) rotates an arced needle in a circular path enabling a surgeon to selectively apply sutures. The circular needle applier (30) may be integral with the shaft (20) and actuator (10) as a unitary disposable instrument intended for a single surgical procedure. The circular needle applier (30) may also be integral with the shaft (20) and actuator (10) as a reusable instrument. Optionally, as illustrated here, the circular needle applier (30) may be embodied in a disposable cartridge (90) and the shaft (20) may include a receiver (50) to hold the cartridge (90). In such an embodiment, the shaft (20) and actuator (10) may also be disposable or reusable. Embodiments with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also used with low temperature sterilization techniques known in the art.

A first input (12), shown here as a trigger that pivots between opened and closed positions, may be used to selectively actuate the circular needle applier (30). The trigger may be spring biased to return the trigger to its open position. A second input (14), shown here as a rotary knob, may be used to selectively articulate the shaft (20). A third input (16), shown here as a rotary knob, may be used to selectively rotate the circular needle applier (30) about the shaft (20). Naturally, the number, type, configuration, and operation of the inputs (12, 14, and 16) may vary.

Examples of surgical suturing devices and subcomponents are disclosed in co-owned U.S. application Ser. No. 13/832,595 filed 15 Mar. 2013, the disclosures of which are incorporated herein by reference. Many of the teachings disclosed in that application are applicable to the present disclosure.

Figure 2A:
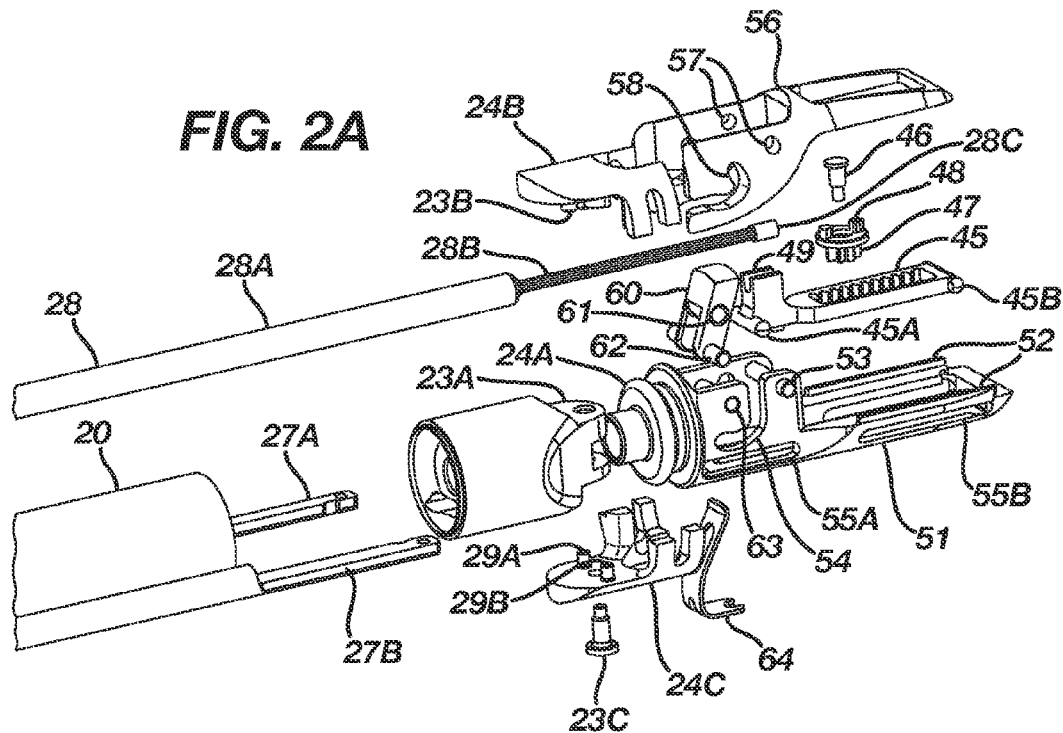
FIG. 2A depicts top perspective exploded view of a receiver.
Figure 2B:
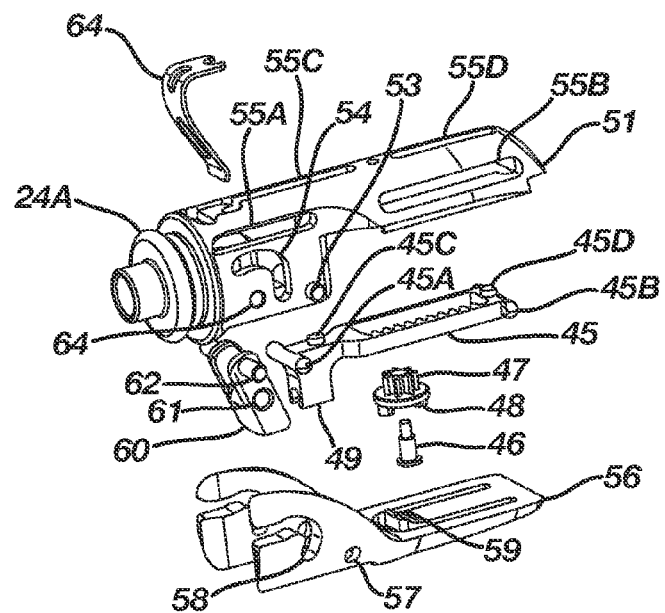
FIG. 2B depicts bottom perspective exploded view of a receiver.

FIGS. 2A-B illustrate exploded views of an embodiment of a receiver (50). The shaft distal end (22) comprises an articulation joint (23) and a rotational bearing (24). The joint (23) includes a knuckle (23A) that receives pins (23B, C) connected to the bearing supports (24B, C). Thus, the pins (23B, C) define the pivoting axis for the joint (23) enabling the receiver (50) to articulate left and right relative the shaft (20). Rods (27A, B) are operably connected to the joint (23). In this embodiment the rods (27A, B) extend through the shaft (20), through the knuckle (23A), and connect to pins (29A, B) on the bearing support (24C). The rods (27A, B) are operatively connected to the second input (14) to alternately push and pull the rods (27A, B). Because the pins (29A, B) are laterally spaced from the pivoting axis, the push and pull action will in turn articulate the receive (50) about the joint (23) relative the shaft (20).

The rotational bearing (24) is positioned distal to the articulation joint (23). The bearing (24) includes a circumferential flange (24A) captured between the bearing supports (24B, 24C) such that the flange (24A) can rotate relative the bearing supports (24B, 24C) and enabling unbounded rotation of the receiver (50) relative the shaft (20). A drive rod (28) extends through the shaft (20). In this embodiment the drive rod (28) comprises a proximal rigid portion (28A) and a distal bendable portion (28B) fixedly connected to one another. The bendable portion (28B) extends through the joint (23) and through the bearing (24), and the distal end (28C) is fixedly connected to the mount (49) on the rack (45).

The rack (45) reciprocates longitudinally in the lower jaw (51) with the followers (45A, B, C and D) constrained in tracks (55A, B, C, and D), respectively. The tracks (55A, B, C, and D) open through the lower jaw (51) providing fluid passages to the internal components within the lower jaw (51), thus facilitating easier cleaning. A pinion (47) is mounted to the lower jaw (51) by the pin (46) in the rack (45) such that longitudinal reciprocation of the rack (45) is translated to rotational reciprocation of the pinion (47). The key (48) translates the reciprocating rotation to the transmission in the cartridge (90), which in turn actuates the circular needle applier (30).

The drive rod (28) is operatively connected to the first input (12) and to the third input (16). Actuation of the first input (12) will impart axial push and pull loads on the drive rod (28) to longitudinally reciprocate the rack (45) and actuate the circular needle applier (30). Actuation of the third input (16) will impart a rotational load on the drive rod (28) thus rotating the receiver (50) about the bearing (24) relative to the shaft (20). Accordingly, a single drive rod (28) operates to both actuate the circular needle applier (30) as well as control distal rotation. By consolidating dual functions with a single drive rod (28), the number of components is reduced, and more space is provided in the shaft (20), making the device less expensive to manufacture and easier to clean.

The receiver (50) is dimensioned and adapted to receive and hold a disposable cartridge (90). The receiver has upper and lower jaws (56, 51) having a closed position adapted receive and retain the cartridge (90) and an opened position adapted to release the cartridge. In this embodiment, the lower jaw (51) is stationary and the upper jaw (56) pivots; however, the arrangement could be reversed, or in an alternative embodiment both jaws (56, 51) could pivot. The lower jaw (51) has two laterally offset longitudinal rails (52) dimensioned and adapted to receive the cartridge (90). The rails (52) help longitudinally align the cartridge (90) in the receiver (50) and laterally retain the cartridge (90) in the jaws (51, 56). The upper jaw (56) pivots relative the lower jaw (51) about the pin (53) that is received in the holes (57). A tooth (59) is resiliently oriented downward from the upper jaw (56) toward the lower jaw (51) with a ramped distal face and a stepped proximal face. The tooth (59) is dimensioned and adapted to latch with the cartridge (90) and longitudinally retain the cartridge in the jaws (51, 56). The tooth (59) deflects by virtue of a resilient cantilevered arm extending proximally from the distal end of the upper jaw (56). In this embodiment the tooth (59) and cantilevered arm are monolithic with the upper jaw (56), thus reducing the number of components and moving pieces, making the device less expensive to manufacture and easier to clean.

The button (60) is used to open and close the jaws (51, 56). While the button (60) could be place on or near the actuator (10), in this embodiment the button (60) is positioned adjacent the receiver (50), which eliminates a linkage in the shaft (20) thus creating space in the shaft (20) and making the device less expensive and easier to clean. The action of the button (60) may vary, but in this embodiment the button (60) pivots relative the lower jaw (51) about the pin (63) that is received in hole (61). The follower (62) is received by the cam slots (54, 58). Pivoting the button (60) proximally will open the jaws (51, 56), while pivoting the jaws distally will close the jaws (51, 56). The spring (64) engages and biases the button (60) distally. By pulling the button (60) proximally, the follower (62) will drive the cam slot (58) to open the upper jaw (56). When the button (60) is released, the spring (64) will bias the button (60) distally to close the upper jaw (56).

Figure 3A:
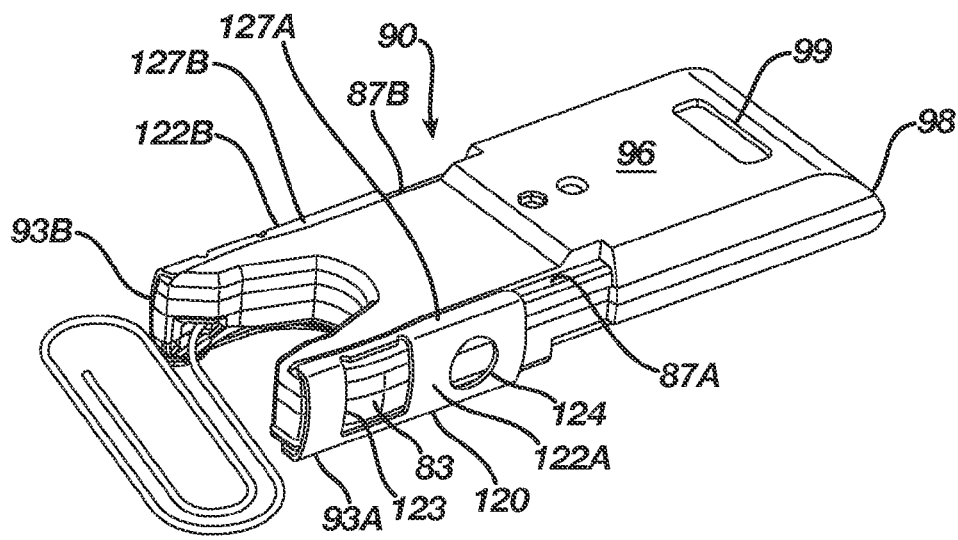
FIG. 3A depicts a scaled top perspective view of a cartridge.
Figure 3B:
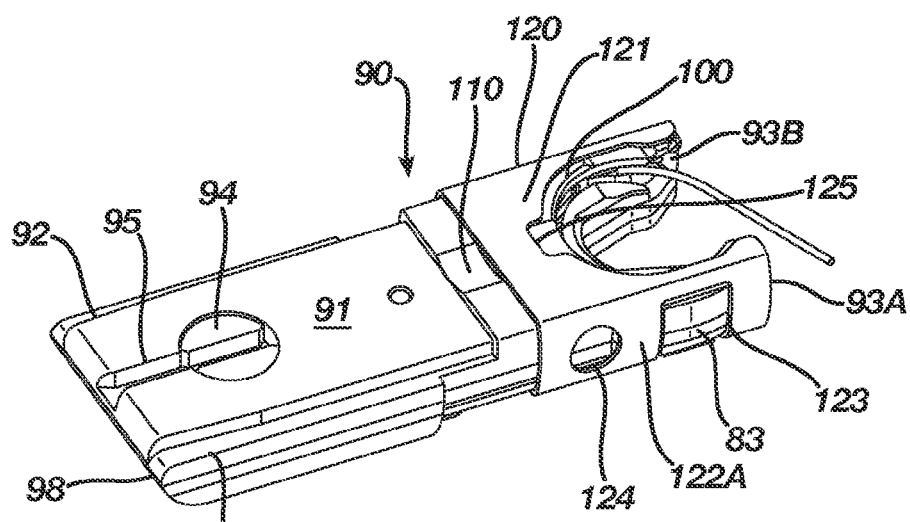
FIG. 3B depicts a scaled bottom perspective view of a cartridge.

FIGS. 3A-B illustrate one embodiment of a disposable needle driver cartridge (90) adapted to be attached to the receiver (50). The upper and lower faces (96, 91) are generally rectangular with a generally U-shaped distal notch. The upper and lower faces (96, 91) are generally flat and parallel to one another. The dimensional ratios of the cartridge (90) may vary based on functional and aesthetic considerations, but in this embodiment the cartridge (90) is elongate with a length at least 2 times the width, and a width less than 3.5 times the height. Optionally, the length may be less than 5 times with width, and the width may be greater than 1.0 times the height.

The lower face (91) is adapted to engage the lower jaw (51) and the upper face (96) to engage the upper jaw (56). Asymmetrical features on the cartridge (90) are operable to prevent improper insertion of the cartridge (90) into the receiver (50), but also contribute to the aesthetic appearance of the cartridge (90). For instance, the lower face (91) has a pair of longitudinal notched shoulders (92) dimensioned to interface and mate with the rails (52). In this embodiment, the notched shoulders (92) are shaped as stepped rabbets, but a variety of other aesthetic shapes could also be employed such as chamfers and radii. In contrast, the upper face (96) is asymmetrical relative the lower face (91) and lacks shoulder notches, so the upper face (96) would interfere with the rails (52) if the cartridge was inserted upside-down. In another instance, the geometry of the proximal face (98) is vertically asymmetrical thus preventing the cartridge (90) from being inserted upside-down between the jaws (51, 56). In this embodiment, the proximal face (98) comprises a curved surface that gently transitions to the upper face (96), which matches similar geometry in the receiver (50), while the transition to the lower face (91) has a tighter radius. Naturally, a variety of other dimensional ratios and asymmetrical aesthetic geometries could also be employed that could contribute to the visual appearance of the cartridge (90).

The slot (95) and rotary input (94) are aligned and dimensioned to receive the key (48) while the cartridge (90) is being slid into the receiver (50). When the cartridge (90) is fully seated into the receiver (50), the recessed step (99) aligns with and receives the tooth (59) to latch the cartridge (90) in the receiver (50). The key (48) also aligns with rotary input (94) thereby providing a torsional interface that rotationally couples the pinion (47) and rotary input (94). In use, the needle (70) exits arm (93A) and enters arm (93B).

Figure 7:
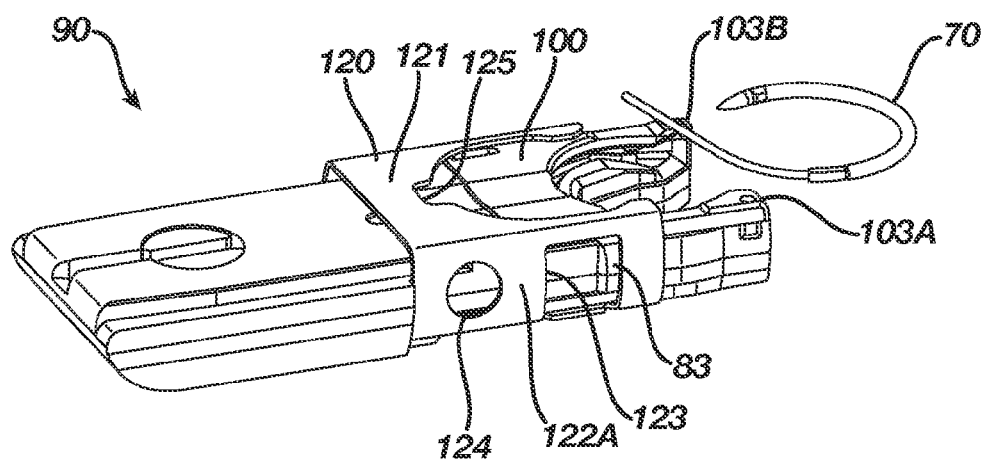
FIG. 7 depicts a scaled perspective view of a cartridge with a cage in its proximal position.
Figure 8:
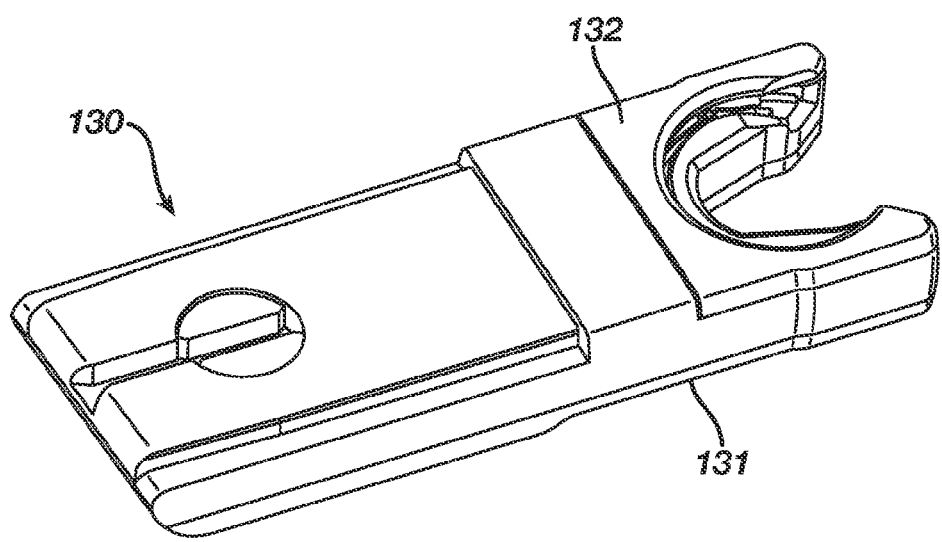
FIG. 8 depicts a perspective view of a cartridge.
Figure 9:
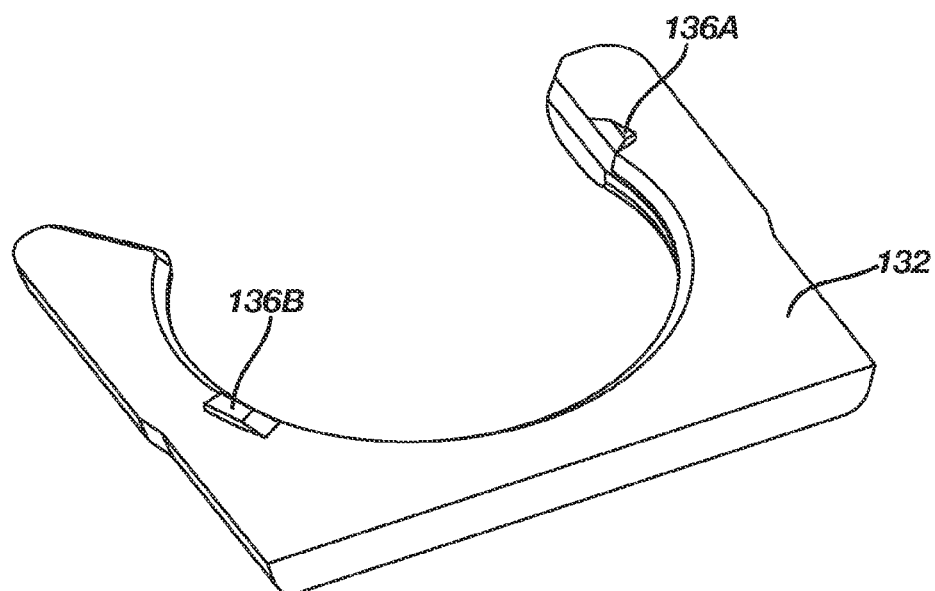
FIG. 9 depicts a perspective view of a needle cover.
Figure 10:
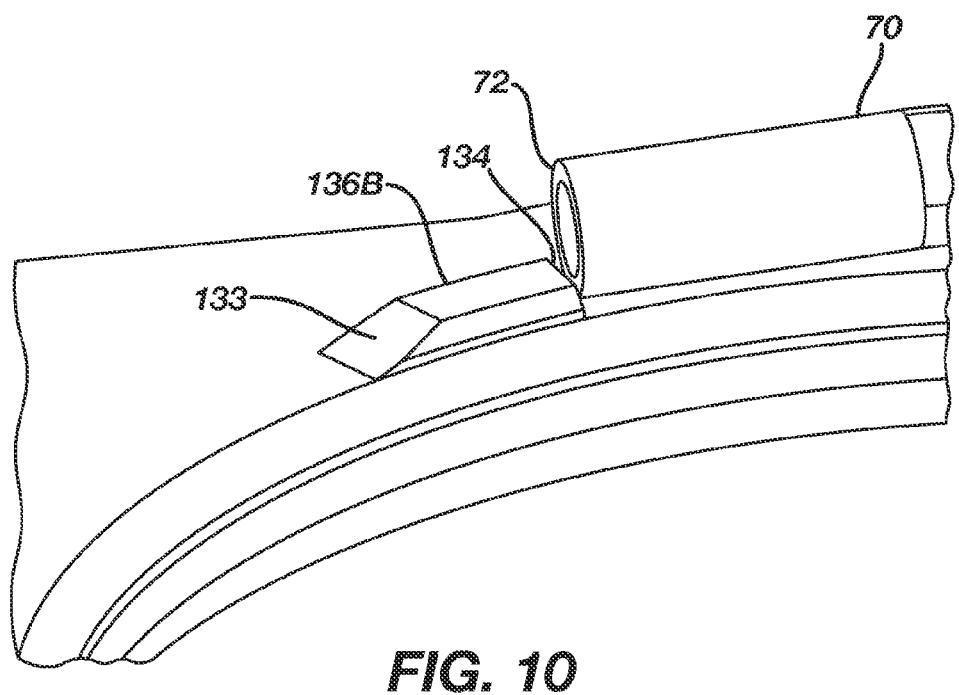
FIG. 10 depicts a detailed view of a cleat engaging a trailing end of a needle.
Figure 11:
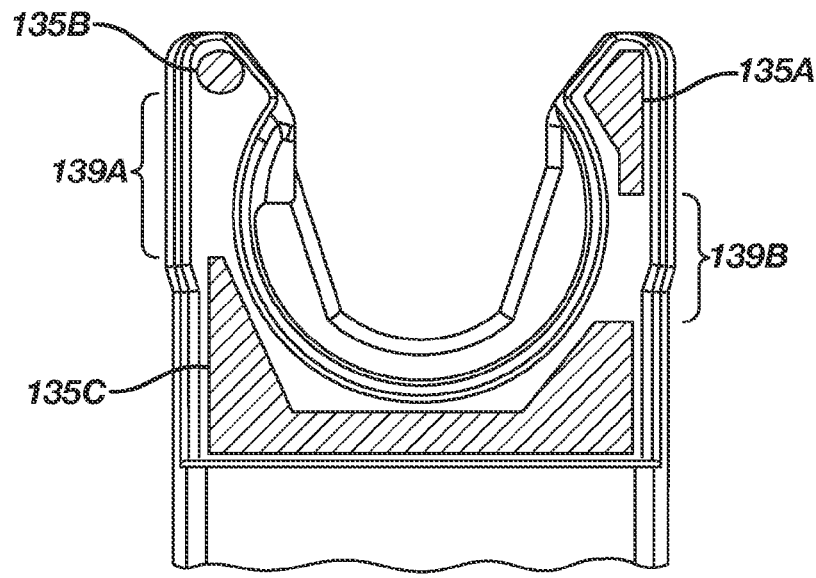
FIG. 11 depicts a plan view of a needle cover.

The cage (120) slides longitudinally on the cartridge (90) between a distal position (as shown in FIGS. 3A-B) and a proximal position (as shown in FIG. 7). The cage (120) may be formed from a sheet of metal stamped and bent to shape, but other materials and manufacturing techniques could also be used. A pair of laterally space legs (122A, B) each include a flange (127A, B) that engages and slides in the stepped notches (87A, B). A bridge (121) extends between the legs (122A, B) that engages and retains the needle cover (100) against the cartridge (90). The bridge (121) includes a distal U-shaped notch aligned with the arms (93A, B). The legs (122A, B) each include an opening (123) that receives a lateral protrusion (83) from the cartridge (90). The protrusions (83) expand the space in the cartridge (90) to accommodate the needle and carrier tracks (84, 88). The protrusions (83) each include a distal ramped portion allowing the cage (120) to slide proximally, and a proximal stepped portion that engages the edge of the openings (123) preventing the cage (120) from sliding distally off the cartridge (90).

Features may be added to facilitate sliding the cage (120). In one example, a recess (125) is provided on the bridge (121) into which a surgeon may insert a surgical instrument to push the cage (120) proximally. The recess (125) aligns with a longitudinal recess (110) to facilitate a more secure engagement between the instrument and the recess (125). In another example, a circular hole (124) extends through each of the legs (122A, B) into which a surgeon may insert a surgical instrument to push the cage (120) proximally. Naturally, the shape, size, and configuration of the features may vary from the foregoing.

Figure 4:
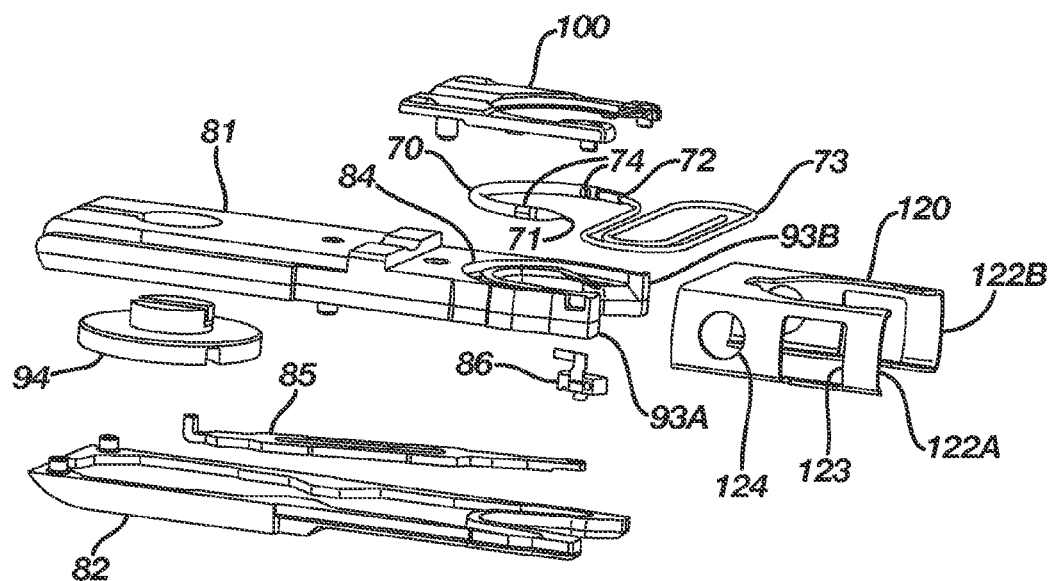
FIG. 4 depicts an exploded view of a cartridge.

FIG. 4 illustrates an example of a cartridge (90) comprising a lower body (81), an upper body (82), and a needle cover (83). The needle driver (86), rotary input (94), and link (85) are captured between the lower body (81) and an upper body (82). The lower and upper bodies (81, 82) are attached to one another using a variety of known techniques, including welds, pins, adhesives, and the like to form the cartridge body. The needle (70) has a leading end (71) and a length of suture (73) extending from the trailing end (72). The needle (70) rotates in a circular path defined by the needle track (84) and between the arms (93A, B). Features (74) may be provided to facilitate the needle driver (86) to engage and drive the needle (70). The needle (70) is captured in the needle track (84) by the needle cover (83). The cage (87) slides over the cartridge body to attach the needle cover (83) against the lower body (81).

Figure 5A:
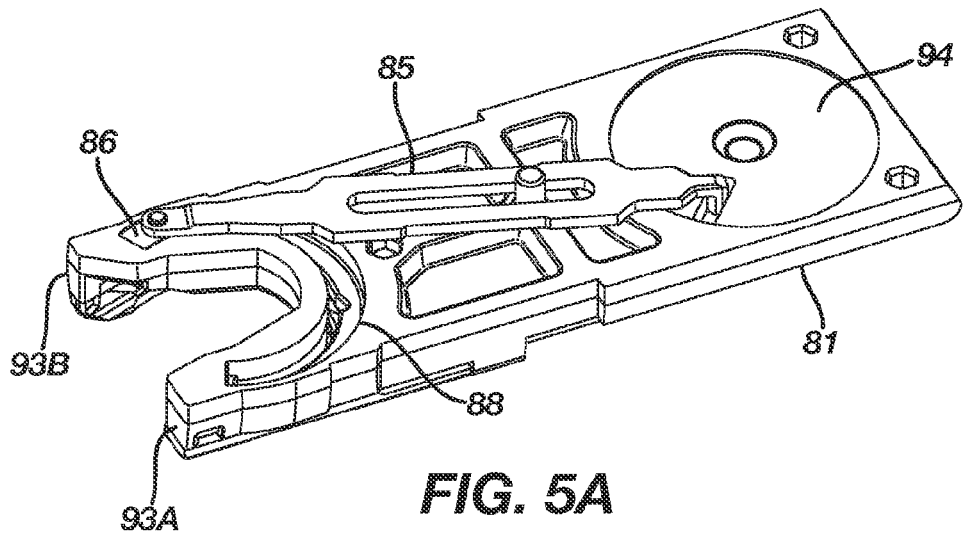
FIG. 5A depicts a perspective view of a transmission for driving a needle at one end of its stroke.
Figure 5B:
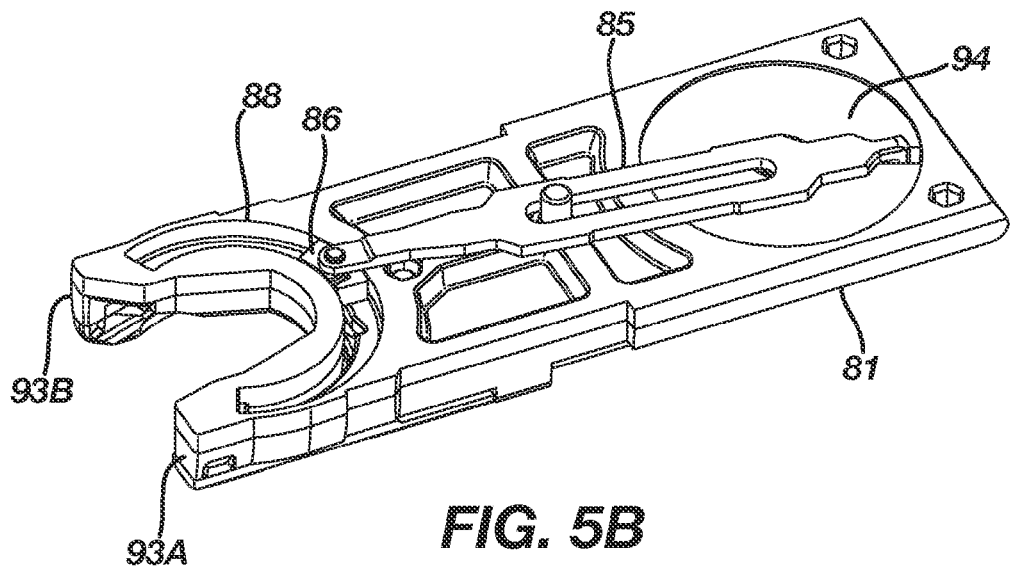
FIG. 5B depicts a perspective view of a transmission for driving a needle at mid-stroke.
Figure 5C:
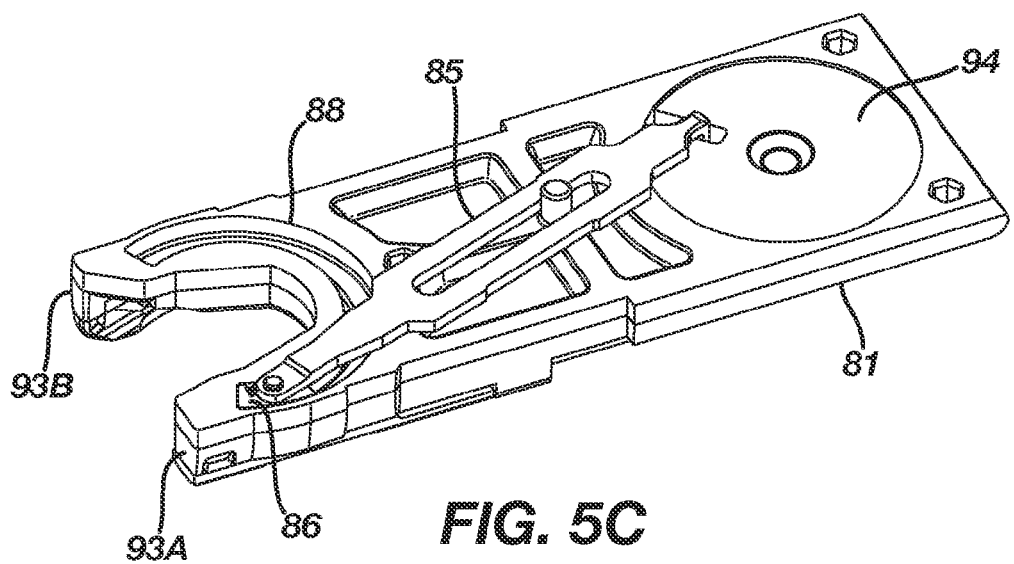
FIG. 5C depicts a perspective view of a transmission for driving a needle at the other end of its stroke.

FIGS. 5A-C illustrate an embodiment of a drive stroke of the transmission in the cartridge (90) for driving a needle (70) in a circular path. The needle driver (86) rides in the carrier track (88) and extends into the needle track (84) to engage and drive the needle (70). A link (85) connects the rotary input (94) to the needle driver (86). FIG. 5A illustrates the needle driver (86) positioned at one end of its stroke in the carrier track (88). As shown in FIG. 5B, counterclockwise rotation of the rotary input (94) will translate the needle driver (86) clockwise along the carrier track (88) driving the needle (70) clockwise. As shown in FIG. 5C, continued counterclockwise rotation of the rotary input (94) will continue to translate the needle driver (86) and drive the needle (70) clockwise until it reaches the other end of its stroke in the carrier track (88). In this embodiment, the drive stroke rotates the needle (70) in its circular path about 180 degrees. For the return stroke, the sequence can be reversed by rotating the rotary input (94) clockwise, which will translate the needle driver (86) counterclockwise in the carrier track (88). Thus, a sequence of drive and return strokes will rotate the needle (70) in a circular path.

Figure 6A:
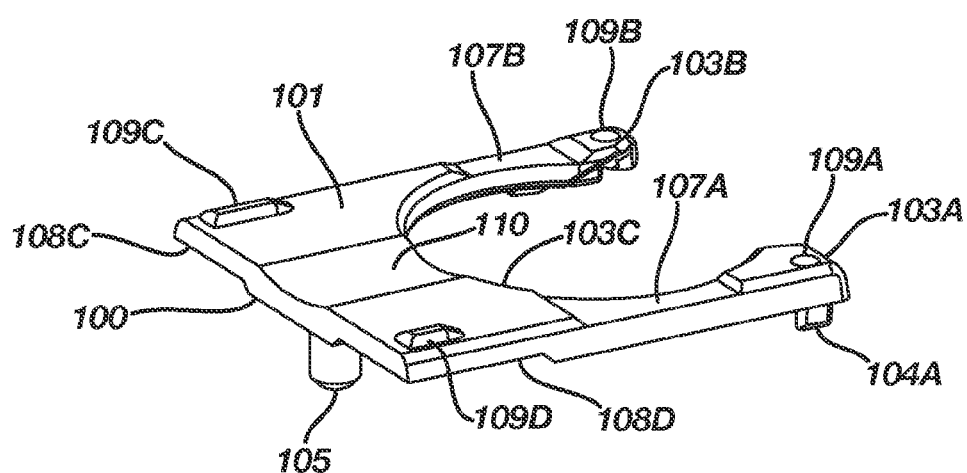
FIG. 6A depicts an outer perspective view of a needle cover.
Figure 6B:
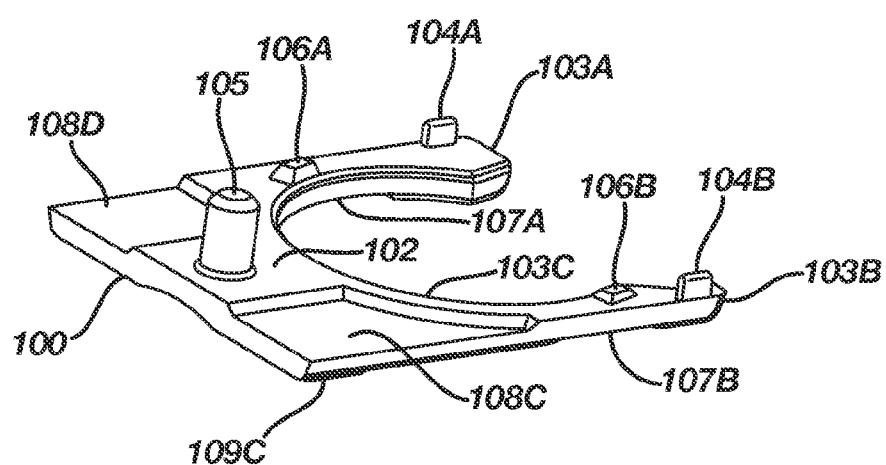
FIG. 6B depicts an inner perspective view of a needle cover.

FIGS. 6A-B illustrate an embodiment of a needle cover (100) having an outer face (101) and an inner face (102) that engages the lower body (81). The arms (103A, B) define a generally U-shaped distal end that aligns with respective arms (93A, B) on the cartridge (90). Tabs (104A, B) facilitate aligning and laterally stabilizing the arms (103A, B) relative the respective arms (93A, B). Post (105) facilitates attaching the cover (100) to the lower body (81), and may have an interference fit with a mating hole on the lower body (81). The cover (100) captures the needle (70) in the needle track (84). The medial edge (103C) partially covers the needle track (84) defining a medial window along the length of needle track (84) through which the suture may extend out. However, the window is dimensioned smaller than the thickness of the needle (70) so as to constrain the needle (70) in the needle track (84).

Cleats (106A, B) extend from the inner face (102) into the needle track (84). While the present embodiment shows the cleats (106A, B) projecting inwardly into the plane of the needle track (84), cleats may be positioned with alternative orientations, such as from the side walls of the needle track (84) or from the floor of the needle track (84). The cleats (106A, B) are positioned so as to be adjacent to the trailing end (72) of the needle (70) at the end of the drive stroke. The cleats (106A, B) allow the needle (70) to rotate during the drive stroke, but engage the trailing end (72) to prevent the needle (70) from rotating in the opposite direction during the return stroke. Accordingly, the needle (70) rotates in only one direction with the leading end (71) going forward. The cleats (106A, B) may dimensionally interfere with the needle (70) in the needle track (84), and may deflect to allow the needle (70) to pass during the drive stoke due to resiliency in the cleat material or the overall system. For instance, this embodiment includes reliefs (107A, B) on the outer face (101) of the cover (100) aligned with the respective cleats (106A, B). The reliefs (107A, B) reduce the cover (100) thickness providing a localized reduction of stiffness and allowing the cover (100) to resiliently deflect to accommodate the interference as the needle (70) passes.

The cleats (106A, B) have multiple advantages compared to other techniques to prevent backward needle rotation, such as leaf springs or pawls. For example, the cleats (106A, B) may be monolithically formed with the cover (100), thus eliminating separate components to advantageously reduce costs and simplify assembly. For instance, the cover and cleats can be injection molded using materials like polycarbonate, polyetherimide, and the like. In another example, the cleats (106A, B) are static thus eliminating moving parts and making the system more robust and reliable. In yet another example, the edges on the cleats (106A, B) tend to be less abrasive thus reducing undesirable wear to the suture (73), especially when compared to a metallic leaf spring.

The bumps (109A, B, C, D) project outwardly from the outer face (101) of the cover (100). The bumps (109A, B, C, D) engage the bridge (121) of the cage (120) with a dimensional interference, thus biasing the cover (100) against the lower body (81). In this embodiment, the distal bumps (109A, B) are shorter than the proximal bumps (109C, D). Reliefs (108C, D) on the inner face (102) aligned with the respective proximal bumps (109C, D). The reliefs (108C, D) reduce the cover (100) thickness providing a localized reduction of stiffness and allowing the cover (100) to resiliently deflect.

As shown in FIG. 7, the cage (120) may be slid proximally relative the cartridge (90) to release the needle (70). In its proximal position, the cage (120) sufficiently disengages with the arms (103A, B) so they are therefore no longer constrained against the lower body (81). Thus, a gentle pull on the needle (70) will cause the arms (103A, B) to deflect away from the lower body (81) allowing the needle (70) to eject from the needle track (84). Optionally, when the cage (120) is pulled proximally the inward load acting on the bumps (109C, D) could rock cover (100) such that the arms (103A, B) lift away from the lower body (81), thus leaving a gap from which the needle (70) could eject.

FIGS. 8-11 illustrate another embodiment of a cartridge (130) having a body (131) and a needle cover (132). Cleats (136A, B) project inwardly and dimensionally interfere with the needle (70) in the needle track (84). Each cleat (136A, B) has a ramped leading face (133) allowing the needle (70) to pass under and deflect the cleat (136A, B) outward during the drive strokes. At the end of the drive stroke the stepped trailing end (73) will rotate past one of the cleats (136A, B) that will then deflect inward. The trailing face (134) will engage with the trailing end (72) to prevent backward rotation of the needle (70). Resiliency in the system allows the cleats (136A, B) to deflect and return. For instance, the needle cover (132) may be secured to the body (131) in zones (135A, B, C) with welds, adhesives, fasteners, snap-fits, and the like. But by leaving the needle cover (131) unsecured in areas (139A, B) aligned with the respective cleats (136A, B), localized resilient outward deflection of the cover (131) may accommodate the dimensional interference as the needle (70) passes.

Figure 12:
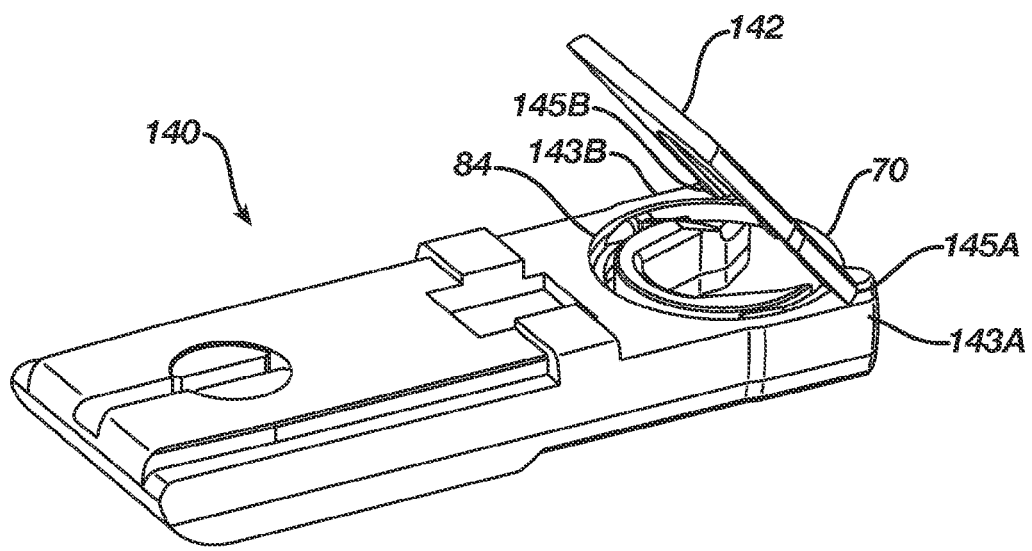
FIG. 12 depicts a perspective view of a cartridge with an opened needle cover.

FIG. 12 illustrates another embodiment of a cartridge (140). The needle cover (142) is connected to the body (141) by hinges (145A, B) on the respective arms (143A, B). The hinges (145A, B) in this embodiment are aligned normal with the longitudinal axis of the cartridge body (141). Snap fits, fasteners, frangible elements, or the like may be used to attach the remainder of the needle cover (142). The needle (70) can be ejected by moving the needle cover (142) away from the body (141) about the hinges (145A, B) to open and expose the needle track (84).

Figure 13:
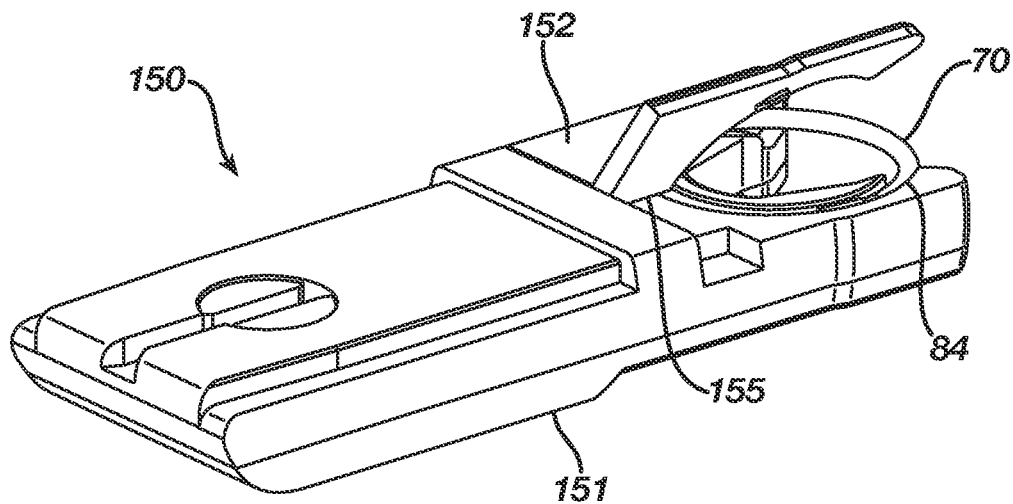
FIG. 13 depicts a perspective view of a cartridge with an opened needle cover.

FIG. 13 illustrates another embodiment of a cartridge (150). The needle cover (152) is connected to the body (151) by a longitudinally oriented hinge (155). In this example the hinge (155) is positioned adjacent the valley of the U-shaped distal end, but could also be located on either lateral side. The needle (70) can be ejected by moving the needle cover (152) about the hinge (155) away from the cartridge body (151) to open and expose the needle track (84).

Figure 14:
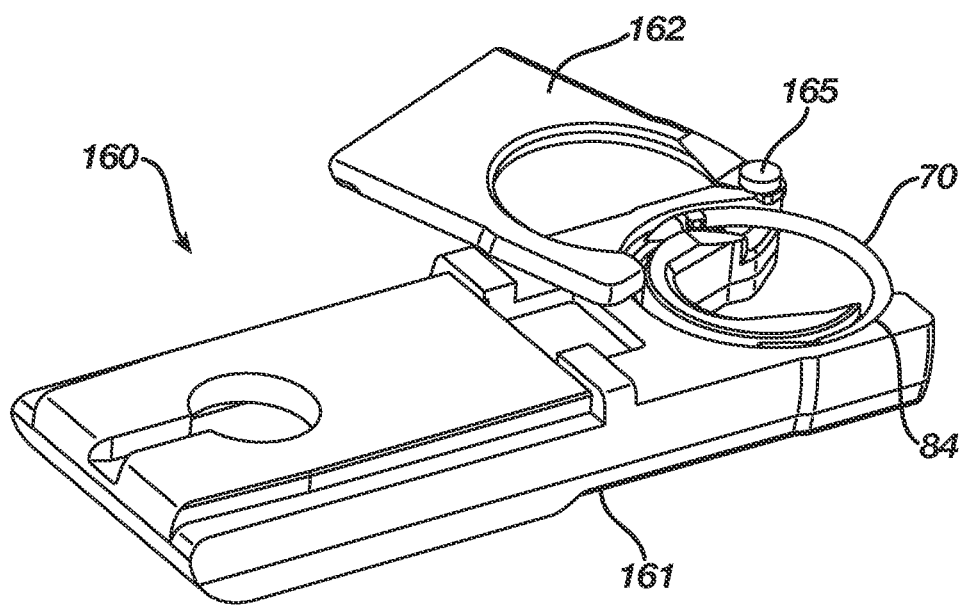
FIG. 14 depicts a perspective view of a cartridge with an opened needle cover.

FIG. 14 illustrates another embodiment of a cartridge (160). The needle cover (162) is connected to the body (161) by a pivot (165) located at the distal end of one of the arms. The needle (70) can be ejected by moving the needle cover (162) parallel with cartridge body (161) about the pivot (165) to open and expose the needle track (84).

Figure 15:
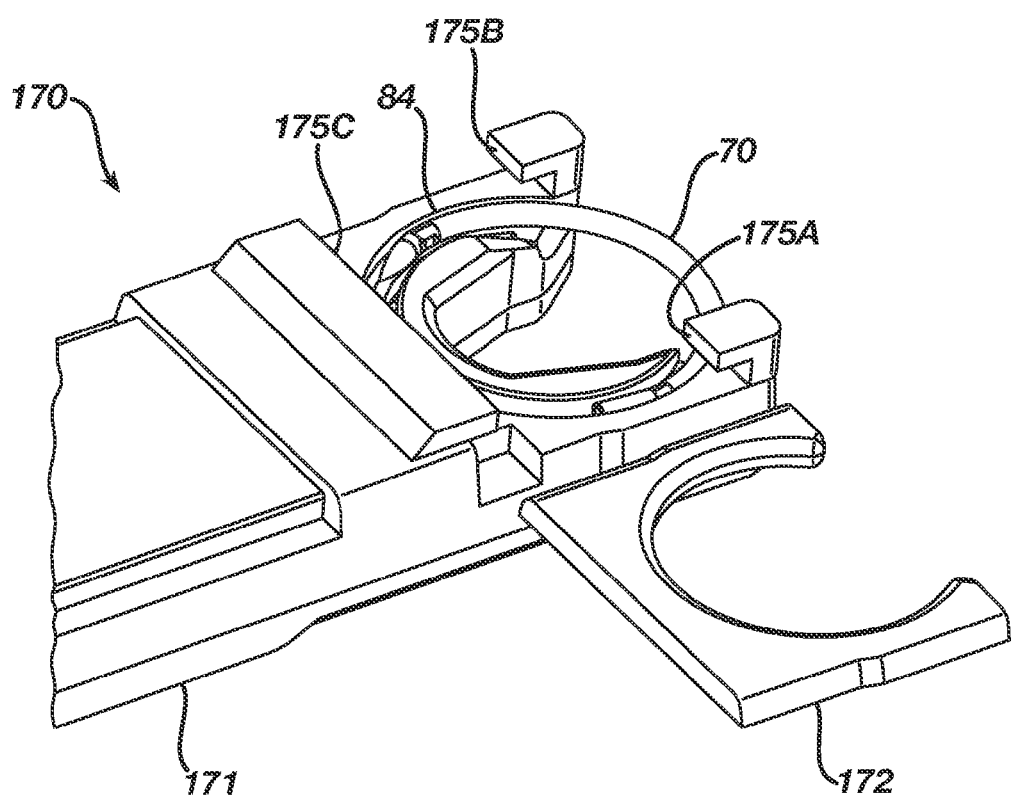
FIG. 15 depicts a perspective view of a cartridge with an opened needle cover.

FIG. 15 illustrates another embodiment of a cartridge (170). The needle cover (172) is connected to the body (171) by retention rails (175A, B, C). The needle (70) can be ejected by moving the needle cover (172) relative the rails (175A, B, C) to open and expose the needle track (84). In this embodiment the needle cover (172) slides laterally, but it could also slide longitudinally or diagonally.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A needle cartridge adapted to be attached to a receiver on a surgical suturing device, the cartridge comprising:
   an arced needle having a leading end, a trailing end, and a length of suture;
   a body having a track receiving the needle and defining a circular path;
   a needle driver operable to rotate the needle along the circular path;
   a cover capturing the needle in the track, the cover having a pair of distally projecting arms; and
   a cage that engages and retains the distally projecting arms of the needle cover against the body;
   wherein the cage slides relative the body to disengage with the distally projecting arms of the needle cover allowing the arms to deflect and release the needle from the track.

2. A needle cartridge adapted to be attached to a receiver on a surgical suturing device, the cartridge comprising:
   an arced needle having a leading end, a trailing end, and a length of suture;
   a body having a pair of distally projecting arms and a track receiving the needle and defining a circular path;
   a needle driver operable to rotate the needle along the circular path across the body arms;
   a cover capturing the needle in the track, the cover having a pair of distally projecting arms aligned with the body arms;
   a cage slideable relative the body between a distal position where the cage constrains the cover arms against the body arms to capture the needle in the track, and a proximal position where the cage disengages from the cover arms allowing the needle to eject from the track, wherein the cover arms deflect to eject the needle.

3. The needle cartridge of claim 2, wherein the body and cover arms define a generally U-shaped distal end, and the cage comprises a U-shaped distal end that aligns with the U-shaped distal end when the cage is in its distal position.

* * * * *